United States Patent [19]
Kathirgamanathan et al.

[11] Patent Number: 4,992,559
[45] Date of Patent: Feb. 12, 1991

[54] POLYMERIZABLE THIOPHENE MONOMERS

[75] Inventors: Poopathy Kathirgamanathan, North Harrow; Martin R. Bryce, Hurst; David Parker, Durham; Nigel R. M. Smith, Packington Nr. Ashby; Andre D. Chissel, Cameron Close, all of United Kingdom

[73] Assignee: Cookson Group plc, London, United Kingdom

[21] Appl. No.: 74,343

[22] Filed: Jul. 16, 1987

[30] Foreign Application Priority Data

Jul. 16, 1986 [GB] United Kingdom ............... 8617358
Nov. 18, 1986 [GB] United Kingdom ............... 8627565

[51] Int. Cl.$^5$ .................. C07D 333/32; C07D 333/36
[52] U.S. Cl. ...................................... 549/65; 526/256; 528/380; 549/63; 549/66; 549/68; 549/76; 549/78
[58] Field of Search ................ 549/66, 65, 63, 64, 549/68, 67, 76, 69, 78, 74, 75

[56] References Cited

U.S. PATENT DOCUMENTS 4,230,872 10/1980 Klaus ................................ 549/62
4,458,086 7/1984 Chekreun ......................... 549/74
4,578,390 3/1986 Jensen ............................... 549/68

OTHER PUBLICATIONS

Chem Abst, 87, 84963y (1977).
Chem Abst, 86, 71494a (1977).

*Primary Examiner*—Christopher Henderson

[57] ABSTRACT

Thiophene derivatives of the formula

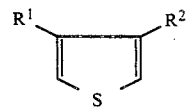

wherein $R^1$ and $R^2$ are certain specified substituent groups can be homopolymerized or copolymerized to form polymers which are electroconductive. These polymers find many uses, for example, as EMI/RF shielding materials, in electrochromic display systems, as antistatics, as ion and pH sensors, as battery electrode materials etc.

7 Claims, No Drawings

POLYMERIZABLE THIOPHENE MONOMERS

The present invention relates to polymerisable monomers based upon a heterocyclic ring system containing sulphur and to the polymerization of these novel monomers.

The Journal of the Chemical Society, Chemical Communications, 1986, pages 1346 and 1347, Kwan-Yue, G. G. Miller and Ronald L. Elsenbaumer, discloses homopolymers and copolymers of 3-alkylthiophenes, such as 3-ethyl-, 3-n-butyl-, 3-n-octyl and 3,4-dimethylthiophene.

We have now discovered certain novel substituted thiophenes which can be polymerized to form conductive polymers.

Accordingly, the present invention provides a compound having the general formula

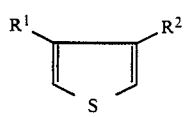

wherein
R$^1$ is —(CH$_2$)$_m$NHCOR, —O(CH$_2$)$_m$NHCOR, —(CH$_2$)$_m$CONHR$^5$, —O(CH$_2$)$_m$CONHR$^5$, —(CH$_2$)$_n$(OCHR$^3$CH$_2$)$_p$OR$^4$, aryloxyalkyl, amino, aminoalkyl or substituted aminoalkyl which is substituted on the nitrogen atom by at least one alkyl, aryl or substituted aryl group;
R is an alkyl group containing from 1 to 18 carbon atoms;
R$^2$ is the same as R$^1$, or is a hydrogen atom, a halogen atom or an amino group.
R$^3$ is a hydrogen atom or a methyl group;
R$^4$ is an alkyl group containing from 1 to 6 carbon atoms;
R$^5$ is an alkyl group containing from 1 to 18 carbon atoms, an aryl group optionally substituted by an alkyl group or an alkylaryl group;
m is an integer of from 1 to 6;
n is 0 or an integer of from 1 to 6;
p is an integer of from 1 to 6.

Preferred compounds of the present invention are those in which the group R$^1$ is —(CH$_2$)$_n$(OCHR$^3$CH$_2$)$_p$OR$^4$ where n is 1 or 2 and p and R$^4$ are as defined above; those in which the group R$^1$ is —CH$_2$NHCOR' where R' is an alkyl group containing from 1 to 12 carbon atoms; or those in which the group R$^1$ is —O(CH$_2$CH$_2$)NHCOR'' where R'' is an alkyl group containing from 6 to 18 carbon atoms. Preferred compounds of the invention are also those in which R$^2$ is a hydrogen atom.

Particularly preferred compounds of the invention are 3-(methoxyethoxymethyl)thiophene, 3-(methoxyethoxyethoxymethyl)thiophene or 3-(butoxyethoxyethoxyethoxymethyl)thiophene, N-(3-thienylmethyl)acetamide, N-(3-thienylmethyl)octanamide or N-(3-thienylmethyl)dodecanamide, 3-(methoxyethoxy)thiophene, 3-(methoxyethoxyethoxy)thiophene and N-(3-O-thienylethoxy)octanamide or N-(3-O-thienylethoxy)dodecanamide.

The thiophene monomers of the invention in which R$^1$ is the group —(CH$_2$)$_n$(OCHR$^3$CH$_2$)$_p$OR$^4$ where R$^3$, R$^4$, n and p are as defined above may be prepared according to the following general reaction scheme:

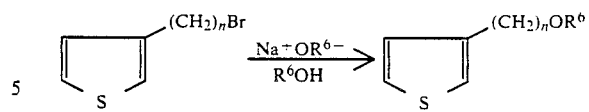

The thiophene monomers of the invention in which R$^1$ is the group —(CH$_2$)$_m$NHCOR where R and m are as defined above may be prepared according to the following general reaction scheme:

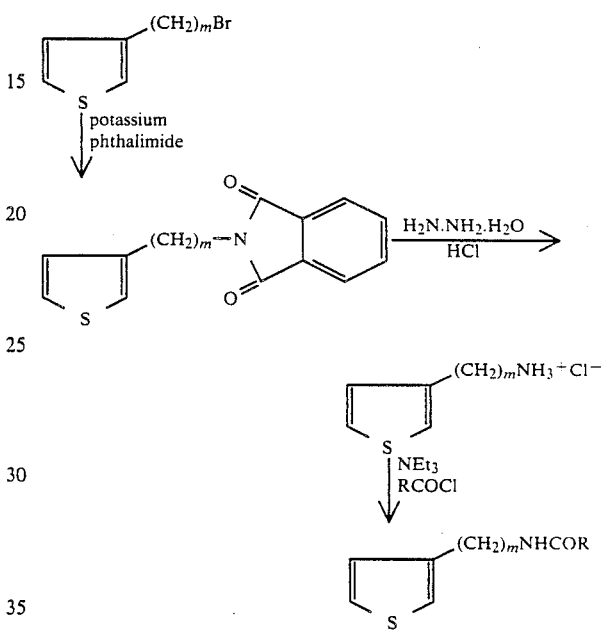

The thiophene monomers of the invention in which R$^1$ is the group —O(CHR$^3$CH$_2$)$_p$OR$^4$ may be prepared according to the following general reaction scheme:

(R$^7$=(OCHR$^3$CH$_2$)$_p$OR$^4$)

The thiophene monomers of the invention in which R$^1$ is the group —O(CH$_2$)$_m$NHCOR where R and m are as defined above may be prepared according to the following general reaction scheme:

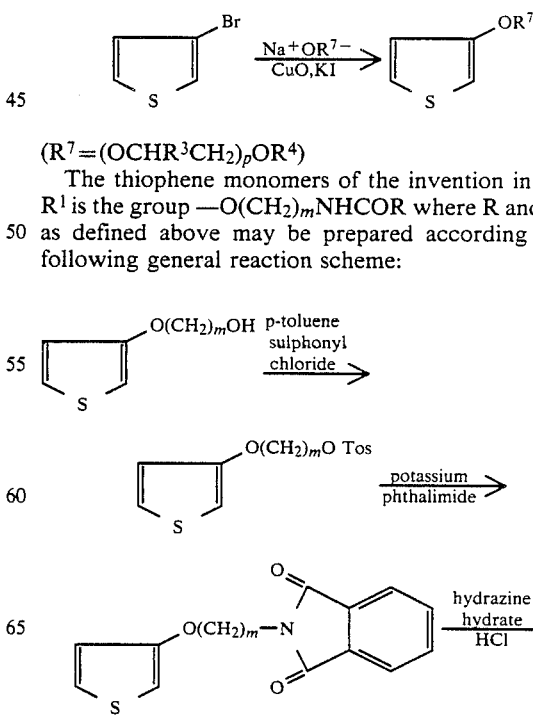

-continued

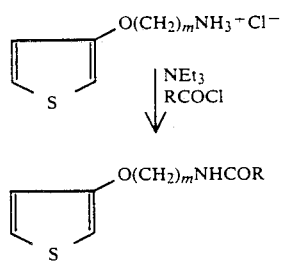

It will be understood that the p-toluene-sulphonyl protecting group may be replaced by any other suitable protecting group.

The thiophene derivatives of the present invention can be polymerized, for example using either an electrochemical or chemical polymerization process, to provide electroconductive polymers.

The electroconductive polymers may be used in thin film technology, as EMI/RF shielding materials, in electrochromic display systems, as antistatic materials, as ion and pH sensors, as battery electrode materials, in switching devices, as protective coatings for electrodes, as electrodes for the selective deposition of metal ions and as self-heating regulators.

For example, in their use as EMI/RF shielding materials the electroconductive polymers may be compounded into conventional polymers to yield conductive plastics materials. Alternatively, the polymers may be formed in situ on a conductive or non-conductive surface to yield a non-corrosive conductive surface. Some soluble electroconductive polymers may be solvent cast onto a surface to provide a conductive sheath, or the electroconductive polymers may be formed by co-electropolymerisation with conventional polymer precursors onto a surface or as a bulk conductive material.

Conductive adhesives may be formed by co-polymerisation of the conductive polymer precursor with an epoxy resin (e.g. Bisphenol A/Bisphenol F/Phenylglycidyl ether) either electrochemically, photochemically or photoelectrochemically.

For use as gas sensors advantage is taken of the changes in conductivity exhibited by the electroconductive polymers on exposure to gases such as CO, NO, $NH_3$, $SO_2$, $C_2H_4$ etc.

For use in display systems electroconductive polymers are chosen which are electrochromic.

The electroconductive polymers can be undoped or doped with cations doped and anions and these properties render them suitable for use in fabricating lightweight battery electrodes.

Alternatively, the monomers may be processed under conditions whereby fibres thereof are formed either on their own or by copolymerising the monomers of the present invention in the presence of one or more co-polymerizable monomers. For example, copolymers may be formed with methyl methacrylate, nylon, styrene, vinyl carbazole or acrylonitrile. Electroconductive fibres are useful in the manufacture of printed circuit boards.

The electrochemical polymerization of the monomers of the invention may be carried out, for example in a single compartment cell using an anode of platinum, indium-tin oxide (ITO), tungsten, titanium, niobium, lead or graphite.

The present invention includes within its scope a process for the preparation of a polythiophene derivative which process comprises subjecting a thiophene monomer as above defined in a non-aqueous solvent to electrochemical oxidation at an electrode potential which is at least as electropositive as the oxidation potential of the thiophene or pyrrole monomer.

The present invention furthermore includes within its scope a polymer which comprises repeating units of the general formula

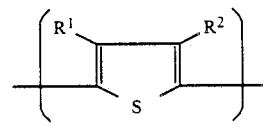

where $R^1$ and $R^2$ are as defined above, and counterions of the formula Z, where Z is chloride, bromide, sulphate, bisulphate, nitrate, tetrafluoroborate, alkylsulphonate, arylsulphonate, arenecarboxylate, alkylcarboxylate, arenedicarboxylate, polystyrenesulphonate, polyacrylate, cellulose sulphonate, cellulose sulphate, anthracene sulphonate, $H_2PO_3^-$, $H_2PO_4^-$, $PF_6^-$, $SbF_6^-$, $AsF_6^-$ or a perfluorinated polyanion.

The electrolyte is chosen so as to provide the counterions as above defined.

The solvent is preferably acetonitrile, dichloromethane, chloroform, nitromethane, nitrobenzene, propylene carbonate, dichloroethane, N-methylpyrrolidone, sulpholane, dimethylformamide or dimethylsulphoxide. The solvent may be used alone or as a mixture of two or more thereof.

The thiophene monomers of the present invention may also be polymerized by chemical means. The chemical polymerization involves the oxidation of the thiophene monomer with an oxidant having a higher standard redox potential than the oxidation potential of the monomer. The oxidation may be carried out in the presence or absence of a catalyst as a single phase or multiphase reaction. Examples of suitable oxidants are $Ag^{II}$, $Cu^{II}$, $Ce^{IV}$, $Mo^V$, $Ru^{III}$, $Mn^{III}$, $H_2O_2$, $K_2Cr_2O_7$ and $(NH_4)_2S_2O_8$. The catalyst may be any transition metal ion, particularly preferred examples of which are $Mo^V$, $Ru^{III}$ and $Mn^{III}$. When a single phase reaction is required the solvent is preferably toluene, dichloromethane, dimethylformamide, chlorobenzene, chloroform or nitrobenzene, or a mixture of two or more thereof. If a multiphase reaction is required an immiscible system can be provided by means of an aqueous layer and an organic solvent layer. The chemical polymerization is preferably carried out at a temperature in the range of from 20° to 110° C. The polymers are either obtained as a thin film at the interface of an immiscible system, or as powders by precipitation, for example with hexane.

The thiophene polymers of the present invention may also be copolymerized with other monomers, for example with pyrrole or thiophene, or any other monomer with which they are copolymerisable, such as styrene and N-vinylcarbazole.

The present invention also includes within its scope a blend of a thiophene polymer as above defined with another polymer, such as, polyvinylchloride, polyethylene, polypropylene, polystyrene, nylon, acrylonitrilebutadiene-styrene, polyethylene terephthalate or polyethylene oxide. The blend will generally contain from 5 to 70% by weight of the thiophene polymer and from 95 to 30% by weight of the other polymer. These blends have good conductivities and good antistatic properties.

The polymers of the present invention may also be directly deposited by chemical oxidative polymerisation or electrochemically onto and/or impregnated into a porous polymer film such as polyvinylchloride. The surface of the composites so-formed is permanently conductive and has good antistatic properties ($\sigma^{sur-face}=10^{-5}$ S □). This surface may be painted with coloured dyes or pigments and the colour modified without impairing the antistatic properties. This method enables antistatic floors and mats to be fabricated from the composites.

Furthermore, non-conductors such as talc and mica may be coated with the polymers of the invention either by chemical oxidative polymerisation or electrochemically. The coated powders are useful as fillers for the formation of conductive polymer composites.

The present invention will be further described with reference to the following Examples.

EXAMPLE 1

Preparation of 3-(methoxyethoxymethyl)thiophene (1)

A solution of 3(bromomethyl)thiophene (6.2 g, 0.035 mol) in carbon tetrachloride (25 ml) was added to a solution of sodium methoxyethoxide (8.9 g, 0.09 mol) in methoxyethanol (90 ml) and the mixture was heated under reflux for 2 hours. After cooling to room temperature, the solvent mixture was removed under reduced pressure and the resultant oil was dissolved in dichloromethane (100 ml), extracted with distilled water ($2 \times 100$ ml) and dried over potassium carbonate. After removal of the solvent, the crude oil was distilled under reduced pressure to yield 3-(methoxyethoxymethyl)thiophene (3.0 g, 50%), B.p. 100°–101° C./10 mm Hg. (Found: C, 55.0; H, 6.3; S, 17.6. Calculated for $C_8H_{12}O_2S$: C, 55.8; H, 7.0; S, 18.6%); EI m/e Intensity (%): 172 (5, M+), 97 (12, $C_4H_3S.CH_2$); $\delta H(CDCl_3)$: 7.05–7.24 (3H, m), 4.53 (2H, s), 3.54 (4H, m) and 3.34 (3H, s); $\delta C(CDCl_3)$: 59.6, 67.0, 69.7, 72.5, 123.4, 126.5, 127.9, 140.0 ppm.

EXAMPLE 2

Preparation of 3-(methoxyethoxyethoxymethyl)thiophene (2)

A solution of sodium methoxyethoxyethoxide (29.6 g, 0.2 mol) in methoxyethoxyethanol (100 ml) was added to a solution of 3-(bromomethyl)thiophene (12.4 g, 0.07 mol) in carbon tetrachloride (25 ml) and the mixture heated under reflux for 12 hours. Work-up as described in Example 1 gave a crude oil which was distilled under reduced pressure to yield 3-(methoxyethoxyethoxymethyl)thiophene (7.0 g, 46%), B.p. 136°–138° C./10 mm. Hg. (Found: C, 56.0; H, 7.0; S, 15.1. Calculated for $C_{10}H_{16}O_3S$: C, 55.5; H, 7.4; S, 14.8%); EI m/e Intensity (%): 216 (12 M+), 97 (100, $C_4H_3S.CH_2$); $\delta H(CDCl_3)$: 6.96–7.17 (3H, m), 4.45 (2H, s), 3.50 (4H, m), 3.40 (4H, m) and 3.26 (3H, s); $\delta C(CDCl_3)$: 58.3, 66.1, 69.2, 70.2, 70.4, 71.7, 121.7, 125.2, 126.7, 139.6 ppm.

EXAMPLE 3

Preparation of 3-(butoxyethoxyethoxyethoxymethyl)thiophene (3)

Butoxyethoxyethoxyethanol (25.0 g, 0.1 mol) was prepared from tetraethylene glycol, sodium hydroxide and butyl chloride (10:1:1) by a method known in the art and then reacted with potassium metal (3.9 g, 0.1 mol) at room temperature for 1.5 hours in tetrahydrofuran. 3-(Bromomethyl)thiophene (17.7 g, 0.1 mol) was added dropwise, and the mixture stirred under reflux for 24 hours. After cooling and filtration the tetrahydrofuran was removed in vacuo and the residue dissolved in methylene chloride, washed with water and dried with potassium carbonate. The solvent was removed and the crude oil distilled to give 3-butoxyethoxyethoxyethoxymethyl)thiophene (25.7 g, 57%). B.p. 162°–163° C./0.15 mm Hg. (Found: C, 58.6; H, 8.7; S, 9.5. Calculated for $C_{17}H_{30}O_5S$: C, 58.9; H, 8.7; S, 9.3%); EI m/e Intensity (%): 346 (9, M+), 97 (100, $C_4H_3S.CH_2$), 57 (75, $C_4H_9$); $\delta H(CDCl_3)$: 7.26 (1H, m) 7.20 (1H, m), 7.06 (1H, m), 4.56 (2H, s) 3.65 (16H, m), 3.45 (2H, t), 1.53 (2H, m), 1.34 (2H, m) and 0.91 (3H, t); $\delta C(CDCl_3)$: 13.6, 18.9, 31.4, 68.1, 69.0, 69.8, 70.0, 70.3, 122.5, 125.5, 126.7, 139.1 ppm.

EXAMPLE 4

Preparation of N-(3-thienylmethyl)acetamide (4)

(A) Preparation of 3-(N-phthalimidomethyl)thiopene

Potassium phthalimide (5.7 g, 0.03 mol) and 18-crown-6-ether (50 mg) were added to a stirred solution of 3-(bromomethyl)thiophene (5.5. g, 0.03 mol) dissolved in N,N-dimethylformamide (70 ml). The mixture was stirred for 3 hours at 80°–90° C. and then cooled and filtered. The filtrate was added to crushed ice (ca. 100 g) and stirred for 5 hours. The resulting solid was collected, dried and recrystallised from absolute ethanol to yield 3-(N-phthalimidomethyl)thiophene (5.2 g, 72%), M.p. 128°–130° C. (Found: C, 64.4; H, 4.0; N, 5.5; S, 13.3. Calculated for $C_{13}H_9NO_2S$: C, 64.2; H, 3.7; N, 5.8; S, 13.2%); EI m/e Intensity (%): 243 (100, M+), 97 (14. $C_4H_3S.CH_2^+$); IR (Nujol): 1690 cm$^{-1}$; $\delta H(CDCl_3)$: 7.65–7.85 (4H, m), 7.15–7.35 (3H, m), 4.84 (2H, s); $\delta C(CDCl_3)$: 36.2, 123.3, 124.2, 126.2, 128.1, 132.1, 134.0, 136.6, 167.8 ppm.

(B) Preparation of 3-(aminomethyl)thiophene hydrochloride

A mixture of hydrazine hydrate (1.4 ml, 0.03 mmol) and 3-(N-phthalimidomethyl)thiophene (6.4 g, 0.026 mol) in absolute ethanol (200 ml) was refluxed for 12 hours. Concentrated hydrochloric acid (5 ml) was then added, and refluxing continued for a further 30 minutes. The solution was then stored at 0° C. for 16 hours, filtered and the filtrate evaporated in vacuo to leave a white solid. This solid was dissolved in distilled water (50 ml), the solution filtered and the filtrate evaporated in vacuo to yield a yellow solid. Recrystallisation from absolute ethanol afforded 3-(aminomethyl)thiophene hydrochloride (3.5 g, 90%) M.p. 165° C. (dec). (Found: C, 40.4; H, 5.0; N, 9.6; S, 21.2. Calculated for $C_5H_8NSCl$: C, 40.1; H, 5.3; N, 9.4; S, 21.4%); $\delta H(D_2O)$: 7.04–7.27 (3H, m), 5.33 (br,s exchanges in $D_2O$), 3.80 (2H, s); $\delta C(D_2O)$: 40.7, 128.5, 130.3, 135.8 ppm.

(C) Preparation of N-(3-thienylmethyl)acetamide (4)

Triethylamine (0.46 g, 4.4 mmol) was added dropwise to a stirred suspension of 3-(aminomethyl)thiophene hydrochloride (0.6 g, 4 mmol) in dry dichloromethane (20 ml) maintained under nitrogen at −5° C. After 15 minutes acetyl chloride (0.31 g, 4 mmol) was added dropwise to the solution which was then stirred for 3 hours at −5° C. After this time the reaction mixture was washed sequentially with dilute HCl (50 ml, 0.5M) and dilute NaOH (50 ml, 0.5 m). The organic layer was separated, dried with magnesium sulphate, and the solvent removed in vacuo to yield the crude product which was recrystallised from hexane to give N-(3-thienylmethyl)acetamide (0.52 g, 85%) M.p. 46°–47° C. (Found: C, 53.5; H, 6.2; N. 8.7, S, 20.4. Calculated for $C_7H_9NOS$: C, 54.2; H, 5.8, N, 9.0; S, 20.7 (%); IR (Nujol): 3250, 1650 cm$^{-1}$; EI m/e Intensity (%): 155 (37, M$^+$), 112 (55, $C_4H_3S.CH_2NH^+$), 97 (29, $C_4H_3S.CH_2^+$). 83 (12, $C_4H_3S$); $\delta H(CDCl_3)$ 7.00–7.29 (3H, m), 6.26 (1H, br,s), 4.41 (2H, d), 1.93 (3H, s); $\delta C(CDCl_3)$: 23.1, 38.7, 122.2, 126.3, 127.3, 139.8, 170.0 ppm.

EXAMPLE 5

Preparation of N-(3-thienylmethyl)octanamide (5)

Using the same reaction conditions as those of Example 4, 3-(aminomethyl)thiophene hydrochloride (4 mmol), triethylamine (4.4 mmol) and octanoyl chloride (40 mmol) were reacted to give N-(3-thienylmethyl)octanamide (0.85 g, 89%). M.p. 71°–72° C. (Found: C, 65.0; H, 8.4; N. 5.7; S, 13.2. Calculated for $C_{13}H_{21}NOS$: C, 65.3; H, 8.8; N, 5.9; S, 13.4%); EI m/e Intensity (%): 239 (19, M$^+$), 97 (63, $C_4H_3S.CH_2^+$); $\delta H(CDCl_3)$ 7.03–7.33 (3H, m), 5.60 (1H, br,s), 4.44 (2H, d), 2.19 (2H, t), 1.61 (2H, m), 1.28 (8H, m), 0.87 (3H, t); $\delta C(CDCl_3)$: 14.2, 22.7, 25.8, 29.1, 29.3, 31.8, 36.9, 38.8, 122.3, 126.5, 127.1, 140.0, 173.1 ppm.

EXAMPLE 6

Preparation of N-(3-thienylmethyl)dodecanamide (6)

Using the same reaction conditions as those of Example 4, 3-(aminomethyl)thiophene hydrochloride (4 mmol), triethylamine (4.4 mmol) and dodecanoyl chloride (4.0 mmol) were reacted to give N-(3-thienylmethyl)dodecanamide (1.1 g, 92%) M.p. 83°–84° C. (Found: C, 68.9; H, 10.2; N, 4.8; S, 10.8. Calculated for $C_{17}H_{29}NOS$: C, 69.1; H, 9.8; N, 4.7; S, 10.9%); EI m/e Intensity (%): 295 (18, M$^+$), 97 (46, $C_4H_3S.CH_2^+$); $\delta H(CDCl_3)$ 7.01–7.30 (3H, m), 5.80 (1H, br,s), 4.46 (2H, d), 2.20 (2H, t), 1.80 (2H, m), 1.25 (16H, m), 0.87 (3H, t);

EXAMPLE 7

Preparation of 3-(methoxyethoxy)thiophene (7)

Sodium (2.0 g, 87 mmol) was added to methoxyethanol (125 ml) under an argon atmosphere. When the sodium had dissolved, a mixture of copper (II) oxide (1.25 g, 16 mmol) and potassium iodide (0.05 g, 0.3 mmol) was added followed by 3-bromothiophene (5g, 31 mmol). The mixture was stirred at 100° C. for three days. Further potassium iodide (0.05 g, 0.3 mmol) was then added and the mixture stirred at 100° C. for a further two days. Chromatography of the crude product on a silica column eluted with diethyl ether gave 3-(methoxyethoxy)thiophene as a colourless oil (3.3 g, 68%). (Found: C, 52.8; H, 6.0; S, 20.1. Calculated for $C_7H_{10}O_2S$: C, 53.1; H, 6.3; S, 20.3%); EI m/e Intensity (%): 158 (25, M$^+$), 100 (26, $C_4H_4OS$), 59 (100, $C_3H_7O$), 45 (50, $C_2H_5O$); $\delta H(CDCl_3)$ 6.23–7.16 (3H, m), 4.07 (2H, t), 3.70 (2H, t), 3.42 (3H, s); $\delta C(CDCl_3)$: 58.9, 69.2, 70.8, 97.2, 119.4, 124.5 ppm.

EXAMPLE 8

Preparation of 3-(methoxyethoxyethoxy)thiophene (8)

Using the same reaction conditions as those of Example 7, sodium (2.0 g) in methoxyethoxyethanol (125 ml), copper (II) oxide (1.25 g), and potassium iodide (0.05 g) were reacted with 3-bromothiophene (5.0 g, 0.031 mmol). Chromatography of the crude product on a silica column eluted with diethyl ether yielded 3-(methoxyethoxyethoxy)thiophene, as a colourless oil (2.1 g, 34%). (Found: C, 53.0; H, 6.8; S, 15.7. Calculated for $C_9H_{14}O_3S$: C, 53.4; H, 6.9; S, 15.9%); EI m/e Intensity (%): 202 (3, M$^+$), 100 (9, $C_4H_4OS$), 59 (53, $C_3H_7O$), 45 (12, $C_2H_5O$); $\delta H(CDCl_3)$ 6.22–7.15 (3H, m), 4.05 (2H, m), 3.76 (2H, m), 3.65 (2H, m), 3.53 (2H, m). 3.34 (3H, s); $\delta C(CDCl_3)$: 58.6, 69.2, 69.4, 70.3, 71.6, 97.2, 119.2, 124.4 ppm.

EXAMPLE 9

Preparation of 3-(hydroxyethoxy)thiophene (9)

Using the same reaction conditions as those of Example 7, sodium (2.0 g) in ethylene glycol (125 ml), copper (II) oxide (1.25 g) and potassium iodide (0.05 g) were reacted with 3-bromothiophene (5.0 g, 0.031 mol). Chromatography of the crude product on a silica column eluted initially with dichloromethane, then with a mixture of dichloromethane/methanol (95:5) yielded 3-(hydroxyethoxy)thiophene, as a white solid (1.9 g, 43%). M.p. 38°–39° C. (Found: C, 49.2; H, 5.3; S, 21.9. Calculated for $C_6H_8O_2S$: C, 50.0; H, 5.6; S, 22.3%); EI m/e Intensity (%): 144 (100, M$^+$), 100 (47, $C_4H_4OS$), 45 (17, $C_2H_5O$); $\delta H(CDCl_3)$ 6.10–7.11 (3H, m), 4.16 (2H, m), 3.84 (2H, m); $\delta C(CDCl_3)$: 60.8, 71.4, 97.7, 119.4, 124.8, 157.4 ppm.

EXAMPLE 10

Preparation of N-(3-O-thienylethoxy)octanamide (10)

(A) Preparation of 3-(toluenesulphonylethoxy)thiophene

Solid p-toluenesulphonyl chloride (0.88 g, 4.6 mmol) was added in small amounts to a cooled (−5° C.) solution of 3-(hydroxyethoxy)thiophene (0.6 g, 4.2 mmol) in dry pyridine (50 ml). The mixture was stirred for 10 minutes and then maintained at −20° C. for 48 hours. The mixture was then stirred with crushed ice for 5 hours. After filtration, the solid was recrystallised twice from hot hexane to give 3-(toluenesulphonylethoxy)thiophene as a white crystalline product, (1.0 g, 83%) M.p. 76°–77° C.; (Found: C, 52.1; H, 4.5; N, 21.8. Calculated for $C_{13}H_{14}S_2O_4$ C, 52.3; H, 4.7; N, 21.5%); EI m/e Intensity (%): 298 (0.5 M$^+$), 199 (57, Tosyl-OCH$_2$CH$_2$); $\delta H(CDCl_3)$ 7.3–7.7 (4H, m), 7.0 (1H, m), 6.5 (1H, m), 6.0 (1H, m), 4.2 (2H, t), 4.0 (2H, t), 2.4 (3H, s); $\delta C(CDCl_3)$: 21.7, 67.5, 68.0, 98.1, 119.3, 125.0, 128.0, 129.9 ppm.

(B) Preparation of 3-N-(phthalimidoethoxy)thiophene 3-(Toluenesulphonylethoxy)thiophene, (0.4 g, 1.4 mmol) and potassium phthalimide (0.3 g, 1.6 mmol) were stirred together at 85° C. for 12 hours with 18-crown-6 ether (50 mg) in dimethylformamide (60 mol). This mixture was cooled to room temperature and stirred into crushed ice for 12 hours. The resulting solid was filtered and recrystallised from absolute ethanol to give a white crystalline product, (0.26 g, 72%) M.p. 146°–147° C.; (Found: C, 62.3; H, 4.1; N, 4.9; S, 11.8.

Calculated for $C_{14}H_{11}NO_3S$: C, 61.5; H, 4.0; N, 5.1; S, 11.7%); EI m/e Intensity (%): 273 (4.1 M+), 174 (100, Phthal- $NCH_2CH_2$); $\delta H(CDCl_3)$ 7.6–7.9 (4H, m), 7.0 (1H, m), 6.6 (1H, m), 6.2 (1H, m), 4.1 (2H, t), 4.0 (2H, t); $\delta C(CDCl_3)$: 37.2, 66.8, 97.9, 119.5, 123.3, 124.7, 132.0, 134.0 ppm.

(C) Preparation of 3-(aminoethoxy)thiophene-hydrochloride

Hydrazine hydrate (0.7 ml, 0.015 mmol) was added slowly to a solution of 3-N-(phthalimidoethoxy)thiophene. (2.6 g, 9.5 mmol) in hot absolute ethanol (200 ml), and the mixture stirred for 12 hours at reflux under nitrogen. Hydrochloric acid (5 ml, conc) was cautiously added to the system and reflux continued for a further 30 minutes. After cooling and filtration, the filtrate was evaporated to dryness to leave a white crystalline solid which was extracted with water. Filtration and removal of the water gave 3-(aminoethoxy)thiophene (1.5 g, 88%). (Found: C, 39.8; H, 5.8, N, 8.1. Calculated for $C_6H_{10}NOSCl$: C, 40.1; H, 5.6; N, 7.8%); $\delta H(CDCl_3)$ 7.1 (1H, m), 6.7 (1H, m), 6.2 (1H, m), 3.9 (2H, t), 3.0 (2H, t); $\delta C(CDCl_3)$: 40.8, 71.5, 96.7, 118.7, 124.1 ppm.

(D) Preparation of N-(3-0-thienylethoxy)octanamide (10)

Triethylamine (1.3 ml, 9.2 mmol) was added over 10 mins to a stirred suspension of 3-(aminoethoxy)thiophene hydrochloride (1.5 g, 8.4 mmol) in dry dichloromethane (60 ml) cooled to −5° C. Octanoyl chloride (1.37 g, 8.4 mmol) in dichloromethane (20 ml) was then added dropwise and stirring continued at −5° C. for four hours. The mixture was then washed with hydrochloric acid (2×50 ml, 0.1M), washed with sodium hydroxide (2×50 ml, 0.1M) and dried with magnesium sulphate. Filtration and solvent evaporation resulted in a white solid which was recrystallised from hot hexane to give N-(3-0-thienylethoxy)octanamide (1.4 g, 62%) M.p. 75°–76° C.; (Found: C, 61.9; H, 8.6; N, 4.9. Calculated for $C_{14}H_{23}NSO_2$: C, 62.4; H, 8.5; N, 5.2%) CI m/e Intensity (%): 270 (0.5, M+), 170 (100, $C_4H_3SOCH_2CH_2NHCO$): IR (Nujol): 3300, 1635 cm$^{-1}$; $\delta H(CDCl_3)$ 7.19 (1H, m), 6.75 (1H, m), 6.27 (1H, m), 5.93 (1H, br, s), 4.02 (2H, t), 3.64 (2H, m), 2.19 (2H, t), 1.63 (2H, t), 1.27 (8H, t), 0.88 (3H, t); $\delta C(CDCl_3)$: 13.8, 22.3, 25.4, 28.8, 29.0, 31.4, 36.4, 38.6, 68.7, 97.5, 116.9, 124.7, 157.0, 173.2 ppm.

EXAMPLE 11

Preparation of N-(3-0-thienylethoxy)dodecanamide (11)

In a similar manner to that described in Example 10 triethylamine (10.0 ml, 6.8 mmol), 3-(aminoethoxy)thiophene hydrochloride (0.8 g, 4.5 mmol) in methylene chloride (20 ml) and dodecanoyl chloride (1.16 ml, 5.0 mmol) in methylene chloride (20 ml) were reacted to give N-(3-0-thienylethoxy)dodecanamide. Recrystallization was from hexane. (Found: C, 66.6; H, 9.9; N, 3.9, S, 9.7. Calculated for $C_{18}H_{31}NO_2S$: C, 66.5; H, 9.5; N, 4.3; S, 9.9%); MPt 97°–98° C.; CI m/e Intensity (%): 326 (7,M+); EI m/e Intensity (%): 226 (100, $CH_3(CH_2)_{10}C(O)N(H)CH_2CH_2$), 126 (5, $C_4H_3S.OCH=CH_2$), 98 (11, $C_4H_3O$); $\delta H(CDCl_3)$ 0.88 (3H, t), 1.24 (16H, br), 1.62 (2H, t, br), 2.19 (2H, t), 3.64 (2H, m), 4.02 (2H, t), 5.98 (1H, br), 6.27 (1H, m), 6.74 (1H, dd) and 7.19 (1H, m); $\delta C(CDCl_3)$: 14.1, 22.6, 25.6, 29.3, 31.8, 36.7, 38.8, 69.0, 97.8, 119.1, 124.9, 173.3 and 184.3 ppm.

EXAMPLE 12

Electrochemical polymerization of thiophene monomers

The electrochemical polymerization of thiophene monomers was carried out in a single compartment electrochemical cell at a temperature of 10° C. under an atmosphere of nitrogen using tetrabutylammonium hexafluorophosphate as the supporting electrolyte. The anode was either platinum or indium-tin oxide (ITO). Direct current conductivity measurements of the polymer films were obtained either while the film was attached to the anode surface (using a two-probe, mercury contact technique) or with a free-standing polymer film that had been peeled off the anode (using a four-probe technique).

The polymerization conditions, which were as detailed above unless otherwise stated, are given in Table 1 below.

The conductivities of some of these polymers are given in Table 2 below.

In both the Tables 1 and 2 the number allocated to the compounds are those used throughout the Specification.

TABLE I

| Compound Number | Method | Concn. of Monomer (M) | Concn. of Bu$_4$NPF$_6$ (M) | Solvent | Condition | Current Density mA cm$^{-2}$ | No. of Coulombs | Colour of the film |
|---|---|---|---|---|---|---|---|---|
| 2 | a | $1.4 \times 10^{-1}$ | $2.5 \times 10^{-2}$ | Nitrobenzene (25 ml) | 10° C. Nitrogen Atmosphere | 1.75 + 0.25 Pt | 1.26 | Copper |
| 2 | b | $2.78 \times 10^{-1}$ | $3.1 \times 10^{-2}$ | Nitrobenzene (25 ml) | 10° C. Nitrogen Atmosphere | 1.65 + 0.15 | 7.43 | Blue-brown |
| 2 | c | $2.32 \times 10^{-1}$ | $2.6 \times 10^{-2}$ | Nitrobenzene (25 ml) | 10° C. Nitrogen Atmosphere | 1.15 + 0.10 | 5.52 | Blue-black |
| 2 | d | $2.32 \times 10^{-1}$ | $2.6 \times 10^{-2}$ | Nitrobenzene (25 ml) | 10° C. Nitrogen Atmosphere | 1.20 + 0.10 | 5.42 | Blue-black |
| 2 | e | $2.41 \times 10^{-1}$ | $4.4 \times 10^{-2}$ | Nitrobenzene (25 ml) | 10° C. Nitrogen Atmosphere | 2.59 + 0.2 Pt | 14.76 | Blue |
| 2 | f | $2.78 \times 10^{-1}$ | $5.2 \times 10^{-2}$ | Nitrobenzene (25 ml) | 10° C. Nitrogen Atmosphere | Current Step of 50 mA for 15 sec then 1.5 + 0.1 | 2.7 | Blue-black |
| 2 | g | $3 \times 10^{-1}$ | $7.5 \times 10^{-2}$ | Nitro- | 10° C. | 1.1 + 0.1 | 0.33 | Green |

TABLE I-continued

| Compound Number | | Concentration (M) | Concentration of supporting electrolyte (M) | Solvent | Condition | Current density mA cm$^{-2}$ | No. of Coulombs | Colour of the film |
|---|---|---|---|---|---|---|---|---|
| 2 | h | | | benzene (25 ml) Nitrobenzene (25 ml) | Nitrogen Atmosphere 10° C. Nitrogen Atmosphere | Pt 1.1 + 0.1 Pt | 2.64 | Green |
| 2 | j | 3.33 × 10$^{-1}$ | 1.24 × 10$^{-1}$ | Nitrobenzene (25 ml) | 10° C. Nitrogen Atmosphere | 2.4 + 0.4 Pt | 4.32 | Green (fibrous deposit) |
| 5 | | 3.8 × 10$^{-2}$ | 5.78 × 10$^{-3}$ | Nitrobenzene/ Dichloromethane (1:1) (30 ml) | 10° C. Nitrogen Atmosphere | 2.5 + 0.1 ITO | 2.25 | Blue-black |
| 6 | a | 8.14 × 10$^{-3}$ | 5.16 × 10$^{-3}$ | Nitrobenzene/ Dichloromethane (1:1) (40 ml) | 10° C. Nitrogen Atmosphere | 15 + 1 Pt | 1.8 | Chocolate brown |
| 6 | b | 2 × 10$^{-2}$ | 5 × 10$^{-3}$ | Nitrobenzene/ Dichloromethane (1:1) (30 ml) | 10° C. Nitrogen Atmosphere | 2.6 + 0.1 Pt or ITO | 3.74 | Black |

| Compound Number | Concentration (M) | Concentration of supporting electrolyte (M) | Solvent | Condition | Current density mA cm$^{-2}$ | No. of Coulombs | Colour of the film |
|---|---|---|---|---|---|---|---|
| 3 | 2.8 × 10$^{-1}$ | tetrabutyl ammonium hexafluoro phosphate 3 × 10$^{-2}$ | nitrobenzene (25 ml) | 10° C. nitrogen atmosphere | 2.45 | 8.82 | Black |
| 2 | 2.8 × 10$^{-1}$ | tetrabutyl ammonium p-toluene-sulphonate 3 × 10$^{-2}$ | nitrobenzene (25 ml) | 10° C. nitrogen atmosphere | 1.75 | 6.3 | Blue-black |
| 2 | 2.8 × 10$^{-1}$ | sodium dodecyl-benzene sulphonate 3 × 10$^{-2}$ | nitrobenzene (25 ml) | 10° C. nitrogen atmosphere | 1.75 | 8.4 | Blue-black |

TABLE 2

| Polymer Compound of Number | Anion | Method Number | $\sigma$/S cm$^{-1}$ |
|---|---|---|---|
| 2 | PF$_6$ | a | 2.03 × 10$^{-2}$ (i), 8 × 10$^2$ (ii) |
| 2 | PF$_6$ | b | 1.05 × 10$^3$ (ii) |
| 2 | PF$_6$ | c | 3.1 × 10$^2$ (ii) |
| 2 | PF$_6$ | d | 3.75 × 10$^2$ (ii) |
| 2 | PF$_6$ | j | 8.5 × 10$^{-5}$ (as a single fibre) |
| 6 | PF$_6$ | a | 1 × 10$^{-2}$ (i) |
| 6 | PF$_6$ | b | 2 × 10$^2$ (ii) |
| 2 | PTS | | 100 (ii) |
| 2 | DDS | | 80 (ii) |
| 3 | PF$_6$ | | 1 × 10$^{-2}$ (ii) |

Footnotes
(i) = 2-probe (ii) = 4-probe
PTS = p-toluenesulphonate DDS = dodecylbenzenesulphonate
Conductivity Measurements
(i) Two Probe:—Two probe conductivity measurement was performed either with two pressure contacts or by the mercury drop method.
(ii) Four Probe:—This was performed by four pressure contacts. A Keithley 228 Voltage/Current source or Thurlby 30V-2A Voltage/Current source was used as a current source. The current was measured with a Keithley 160 digital multimeter and voltage monitored by a Keithley 195A digital multimeter.

EXAMPLE 13

Chemical polymerization of
3-(methoxyethoxymethyl)thiophene 3-(Methoxyethoxymethyl)thiophene (1.0 g) was layered on top of a solution of Mo$^V$Cl$_5$ (0.5 g) in 30 ml of chloroform. The top layer darkened to give a blood red solution on standing for one hour. The top layer was carefully siphoned off and, on addition of n-hexane, a black powder precipitated which had a volume conductivity of 1×10$^{-3}$ S cm$^{-1}$ (compacted disc). When an n-butyl acetate solution of the poweder was reconstituted as a film, a surface conductivity of 2.21×10$^{-5}$ S □ was obtained.

EXAMPLE 14

Chemical polymerization of
3-(methoxyethoxymethyl)thiophene

The method employed was similar to that of Example 13 but the biphasic system was left to stand for 24 hours as the colouration, which indicated the formation of a polymer, was slower. The powder precipitated had a volume conductivity of 5×10$^{-2}$ S cm$^{-1}$ (compacted disc)

EXAMPLE 15

Chemical polymerization of
3-(methoxyethoxyethoxymethyl)thiophene

A solution containing 3-(methoxyethoxyethoxymethyl)thiophene (0.5 g) in toluene (25 ml) was layered onto a solution containing (NH$_4$)$_2$S$_2$O$_8$ (10 g), Mn$^{III}$-(OAc)$_3$(0.1 g) and p-toluenesulphonic acid (10 g) in 25 ml of water. The solution was then stirred at 60° C. so that both the aqueous and non-aqueous phases mixed thoroughly and was then left to stand for 24 hours. A black precipitate was formed which was filtered, washed with water and a small amount of acetone and then with n-hexane. The volume conductivity was $1.1 \times 10^{-2}$ S cm$^{-1}$. When a solution of this black powder in acetone was applied to a microscope slide, the thin layer had a surface conductivity of $1.4 \times 10^{-10}$ S □ and a volume conductivity of $1.4 \times 10^{-6}$ S cm$^{-1}$.

EXAMPLE 16

Chemical polymerization of 3-(methoxyethoxyethoxymethyl)thiophene

A nitrobenzene solution (50 ml) containing 10 g of 3-(methoxyethoxyethoxymethyl)thiophene, 0.2 g of Mn$^{III}$(OAc)$_3$, and 10 g of Ce$^{IV}$ stearate was heated to 110° C. for 4 hours with mechanical stirring and nitrogen bubble agitation. The solution was then allowed to stand for 24 hours. The yellow brown precipitate was treated with n-hexane and filtered at suction and dried at 40° C. in vacuum. On doping the polymer obtained with iodine (vapour), a volume conductivity of $10^{-6}$ S cm$^{-1}$ was obtained.

EXAMPLE 17

Chemical polymerization of 3-(methoxyethoxyethoxyethoxy)thiophene 3-(Methoxyethoxyethoxymethyl)thiophene (1.0 g) and Mn$^{III}$(OAc)$_3$(1.0 g) were dissolved in 50 ml of dichlormethane. The solution was left to stand when a black precipitate was formed. This precipitate was treated with n-hexane and the black powder was washed with hexane and acetone. A suspension of the black powder was layered on to a glass microscope slide and the solvent was evaporated off at room temperature. A surface conductivity of $2.21 \times 10^{-9}$ S □ and a volume conductivity of $2.21 \times 10^{-5}$ S cm$^{-1}$ was observed.

EXAMPLE 18

Co-polymerization of pyrrole and 3-(methoxyethoxyethoxymethyl)thiophene

Pyrrole (3.0 g) and (9.0 g) 3-(methoxyethoxyethoxymethyl)thiophene were mixed with toluene and the mixture was layered onto an aqueous solution (50 ml) containing (NH$_4$)$_2$S$_2$O$_8$ (10 g) and poly(sodium-4-styrenesulphonate) (12.0 g 20% wt % solution in water). An immediate black precipitate was obtained. This precipitate was washed with water, acetone, hexane and then with acetone and dried at 70° C. in vacuum to a constant weight. The volume conductivity of the product was 1 S cm$^{-1}$.

EXAMPLE 19

Formation of Conductive Blends

A 15% (by weight) solution of polyvinylchloride (unplasticized, powdered, Corvic S68/173) in a mixture of solvents comprising 40% tetrahydrofuran, 10% methyl ethyl ketone, 25% dimethylformamide and 10% cyclohexanone was applied to a platinum electrode (1 cm × 3 cm) and left to dry at room temperature for 2 days. The electrode was immersed into an undivided cell containing 9.26 mmoles of 3-(methoxyethoxyethoxymethyl)thiophene and 1.29 mmoles of tetrabutyl ammonium hexafluorophosphate in nitromethane (30 ml) and electrolysed at a current density of 6.67 mA cm$^{-2}$ for 1 minute and at a current density of 2.3 mA cm$^{-2}$ until the total charge passed was 25.8 C whence a rose coloured elastic film was formed. This film was washed with n-hexane and air dried.

Based on the weight of the composite, number of coulombs passed and current efficiency, the weight percent of the thiophene polymer in the polyvinylchloride was 8.1%.

The films so obtained had surface conductivities in the range $1.1 \times 10^{-5}$ S □ to $2 \times 10^{-4}$ S □ and volume conductivities in the range of from $1 \times 10^{-3}$ S cm$^{-1}$ to 2 S cm$^{-1}$.

EXAMPLE 20

Formation of Conductive Blend

A platinum electrode was coated with polyvinylalcohol (86.5–89% hydrolysed) and electrolysis carried out in a 0.1M solution of (3-methoxyethoxyethoxymethyl)-thiophene in acetonitrile (Bu$_4$NPF$_6$=0.05M) at a current density of 5 mA cm$^{-2}$ for 1 hour. A brown film was formed which had a surface conductivity of $1.94 \times 10^{-7}$ S □ and a volume conductivity of $5.24 \times 10^{-5}$ S cm$^{-1}$.

EXAMPLE 21

Electrochemical formulation of an Antistatic Resin 3-(Methoxyethoxyethoxymethyl)thiophene (10 g) in 20 ml of polyacrylic acid (molecular weight 230,000) was electrolysed at a current density of 3.25 mA cm$^{-2}$ for 8.3 hours under a nitrogen atmosphere. The slurry was then stirred for ½ hour at 55° C. The resin was then hardened by heating to 80° C. for 2 hours in an air circulating oven and the hardened resin was then applied as a coating or a strip onto a microscope slide and then further hardened at 80° C. for 2 hours, or 100° C. for 1 hour.

The conductivities of the lightly coloured semi-transparent films are given in Table 3 below:

TABLE 3

| Temperature of hardening | Surface Conductivity $\sigma^S$/S □ | Volume Conductivity $\sigma^V$/S cm |
|---|---|---|
| 80° C. for 2 h. | $2.6 \times 10^{-6}$ | $1.2 \times 10^{-5}$ |
| 100° C. for 1 h. | $2.6 \times 10^{-6}$ | $1.2 \times 10^{-5}$ |
| 100° C. for 6 h. | $6.7 \times 10^{-9}$ | $7.4 \times 10^{-7}$ |

The estimated loading of the thiophene polymer in the above resin is not more than 5% by weight.

This high conductivity enables the resin to be used as an antistatic paint.

EXAMPLE 22

Electrochemical co-polymerization of thiophene

In a manner similar to that of Example 12, thiophene monomers were co-polymerized with other monomers according to the conditions which are detailed in Table 4 below.

TABLE 4

| Compound Number and co-monomer | Concn. of Monomer (M) | Supporting electrolyte Bu₄NPF₆ (M) | Solvent | Condition | Current Density mA cm$^{-2}$ | No. of Coulombs | Colour of the film |
|---|---|---|---|---|---|---|---|
| 2 + styrene | 0.685 1.150 | 0.243 | nitrobenzene (25 ml) | 10° C. nitrogen atmosphere (Pt) | 5 | 72 | Black |
| 2 + N-vinyl carbazole | 0.347 0.129 | 0.101 | nitrobenzene (30 ml) | 10° C. nitrogen atmosphere (Pt) | 2.5 | 36 | Blue-black |
| 2 + N-vinyl carbazole | 0.329 0.259 | 0.405 | nitrobenzene (45 ml) | 10° C. nitrogen atmosphere (ITO) | 1 | 14.4 | Green |
| 2 + N-vinyl carbazole | 0.232 0.086 | 0.27 | nitrobenzene (45 ml) | 10° C. nitrogen atmosphere (ITO) | 1 | 14.4 | Green |

The conductivities of the electroco-polymerized polymers are given in Table 5 below. The conductivities were all measured by the 4-probe method described above in relation to Example 12.

TABLE 5

| Polymer of Monomer and comonomer | Method | Anion | $\sigma$/S cm$^{-1}$ |
|---|---|---|---|
| 2 + styrene | | BF₄ | $2 \times 10^{-3}$ |
| 2 + vinyl carbazole | a | BF₄ | $7 \times 10^{-2}$ |
| 2 + vinyl carbazole | c | BF₄ | $1.5 \times 10^{-2}$ |

The copolymer [(methoxyethoxyethoxymethyl)thiophene-vinyl carbazole]$_n$BF₄ produced by method (c) is a transparent green material. It is useful as a transparent green antistatic material or an EMI/RF± shielding material. This polymer is soluble in n-butylacetate and methyl butyl kerone and the reconstituted green film has only a slightly reduced conductivity.

We claim:

1. A compound having the general formula

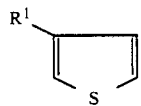

wherein
R¹ is selected from the group consisting of —(CH₂)$_m$NHCOR, —O(CH₂)$_m$NHCOR, [—CH₂)$_m$CONHR⁵][—O(CH₂)$_m$CONHR⁵][—O(-CH₂)$_n$O(CHR³CH₂)$_p$OR⁴]—(CH₂)$_n$(OCHR³CH₂)$_p$OR⁴ and aryloxyalkyl;
R is an alkyl group containing from 1 to 18 carbon atoms;
R³ is selected from the group consisting of a hydrogen atom and a methyl group;
R⁴ is selected from the group consisting of an alkyl group containing from 1 to 6 carbon atoms;
R⁵ is selected from the group consisting of an alkyl group containing from 1 to 18 carbon atoms, an aryl group optionally substituted by an alkyl group and an alkylaryl group;
m is an integer of from 1 to 6;
n is selected from the group consisting of 0 and an integer of from 1 to 6;
p is an integer of from 1 to 6.

2. A compound according to claim 1 wherein the group R¹ is selected from the group consisting of [—CH₂)$_n$(OCH₂CH₂)$_p$OR⁴] where n is 0 or 1 and p and R⁴ are as defined in claim 1; —CH₂NHCOR' where R' is an alkyl group containing from 1 to 12 carbon atoms; and —O(CH₂CH₂)NHCOR'' wherein R'' is an alkyl group containing from 6 to 18 carbon atoms.

3. 3—(Methoxyethoxyethoxymethyl)thiophene.
4. N—(3-thienylmethyl)octanamide.
5. 3—(Methoxyethoxyethoxy)thiophene.
6. N—(3-0-thienylethoxy)octanamide.
7. 3—(Methoxyethoxymethyl)thiophene.

* * * * *